United States Patent [19]

Williams, Jr.

[11] Patent Number: 4,641,642
[45] Date of Patent: Feb. 10, 1987

[54] PATIENT-ACTIVATED BODY IMMOBILIZER AND METHOD OF USE

[76] Inventor: Glenn A. Williams, Jr., 795 Carmel Ave. #3, Sunnyvale, Calif. 94086

[21] Appl. No.: 632,713

[22] Filed: Jul. 19, 1984

[51] Int. Cl.[4] .............................................. A61F 5/37
[52] U.S. Cl. ...................................... 128/134; 128/96; 128/78; 2/44
[58] Field of Search ................. 128/78, 96, 134; 2/44, 2/45, 338

[56] References Cited

U.S. PATENT DOCUMENTS

| 352,010 | 11/1886 | Shelby | 2/309 |
| 2,563,766 | 8/1951 | Weinstein | 119/96 |
| 2,723,664 | 11/1955 | Davis | 128/78 |
| 2,815,752 | 12/1957 | Forman | 128/28 |
| 3,346,930 | 10/1967 | Browning | 2/338 |
| 4,390,014 | 6/1983 | Forman | 128/78 |

FOREIGN PATENT DOCUMENTS

| 1575257 | 7/1969 | France | 128/134 |
| 2089217 | 6/1982 | United Kingdom | 128/78 |

Primary Examiner—Clyde I. Coughenour
Attorney, Agent, or Firm—Flehr, Hohbach, Test, Albritton & Herbert

[57] ABSTRACT

A temporarily immobilizing harness is loosely positioned about the chest or other body part and closely spaced handles are squeezed using one or both hands to tighten the harness about the body. The harness is useful, for example, for restraining the chest against expansion during bouts of coughing or sneezing following open heart surgery.

6 Claims, 13 Drawing Figures

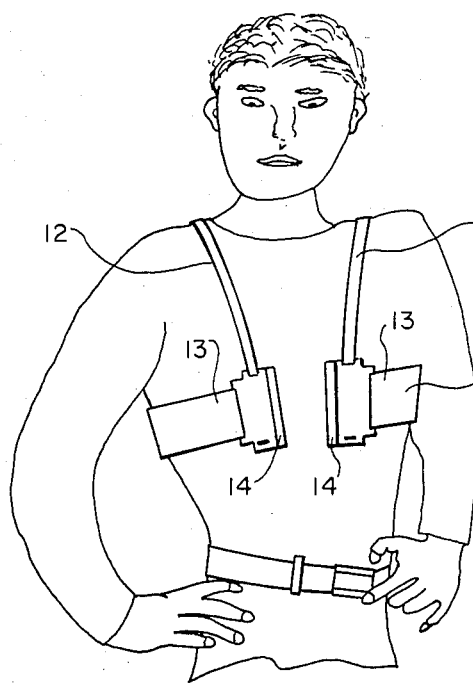
FIG.—1
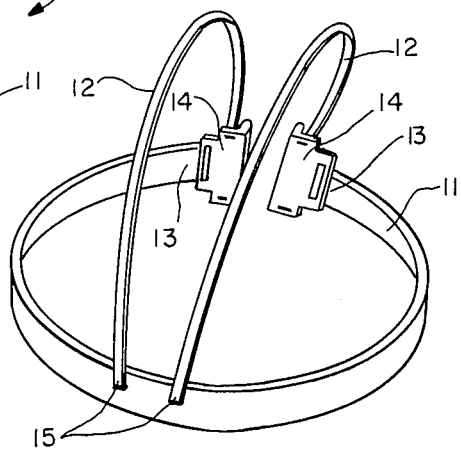
FIG.—2
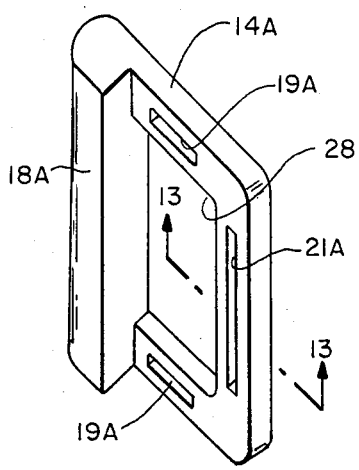
FIG.—12
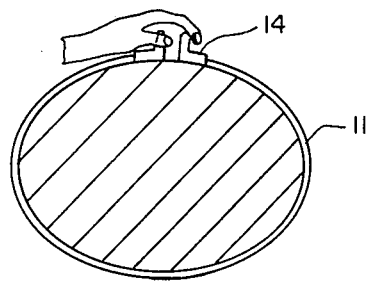
FIG.—3
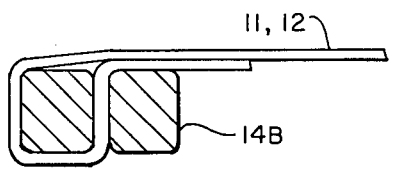
FIG.—13

PATIENT-ACTIVATED BODY IMMOBILIZER AND METHOD OF USE

BACKGROUND OF THE INVENTION

The present invention relates to a harness or restraint, and to a method of using same, for temporarily immobilizing a patient's chest cavity or abdomen (or other body part) to relieve the strain which orrurs, for example, during periods of chest expansion or other movement. Specifically, the harness of the invention (1) is designed to provide a comfortable, snug fit during periods of relaxation, yet (2) is readily gripped and tightened using one or both hands to firmly encase the body during periods of movement or expansion such as those caused by coughing or sneezing. The use of the harness involves squeezably engaging mating end grips to temporarily tighten the harness about the effected body part.

Operations or injuries to the abdomen or upper body cavity frequently involve great trauma to muscle, tissue and/or bone. For example, merely gaining access to the heart cavity for heart surgery may involve cutting the sternum lengthwise using a power saw, in addition to cutting through tissue. This is in addition to the possibly extensive surgery to the heart muscle and connecting arteries and veins.

After the operation, the sternum is wired together, but for approximately 3 to 6 weeks, the patient suffers considerable pain. The pain is even worse when the patient moves, for example, when the chest expands during coughing or sneezing. Unfortunately, considerable congestion occurs during the recovery period and it is recommended that the patient cough as much as possible in order to remove fluid from the lungs, since post-operative pneumonia is a danger. Thus, the problem is that the patient must cough to avoid pneumonia, but coughing or sneezing causes excruciating pain due to the expansion of the chest cavity and the stress and strain on the healing sternum and tissue.

Various medical and safety harnesses are available which provide encircling support or restraint of body parts. For example, Hasslinger U.S. Pat. No. 4,396,013 teaches a harness for supporting and guiding an ambulatory patient comprising a strap which is securely belted about the body by Velcro TM fasteners. The harness includes a pair of handles or loops to permit an attendant to support and guide the movement of the patient. Simpson U.S. Pat. No. 4,273,130 discusses various types of medical constrictors which are used to control the circulation of blood. These include a strip of flexible material having projections along one section which fit into openings in an overlapping section. Velcro TM fasteners can be attached to the opposite ends of the constrictor strap. In the particular construction which is the subject of the Simpson patent, an elongated, flexible constrictor strip is used which has a ring fastened at one end. An end tab at the other end loops through the ring and is folded back to overlap and attach to the strap body via Velcro TM coupling surfaces or adhesive-type surfaces.

Kilmer U.S. Pat. No. 2,900,976 discloses a device for elevating an impaired limb, comprising a leg-encircling band which is raised and lowered by a pulley-supported cable. The band includes a flexible string which has a first ring at one end and a D-ring at the second end which passes through the first ring and attaches to the cable for encircling and elevating limb. Finally, DeMeo U.S. Pat. No. 3,487,474 discloses a safety belt which provides a handhold for passengers riding behind motorcycle drivers.

The adjustable link belt encircles the waist of the driver; the safety gripping feature is provided by a pair of hand grips or loops at the rear of the belt.

One problem with the above-described representative harnesses with respect to the need for a temporary immobilizer is that they are designed to securely restrain encircled body part without regard to quickness of application or release. Use of such harnesses as a chest or sternum splint would involve essentially continuous wear since it is not possible to quickly apply the device in anticipation of, or at the onset of coughing. However, continuous wear is contrary to the medical recovery technique of leaving the chest unbound to reduce the possibility of post-operative pneumonia.

The need for a temporary chest immobilizer which can be applied instantaneously was realized as the result of personal experience with surgery, the level of pain involved during the post-operative recovery process and the lack of available techniques and aids for effectively immobilizing the chest cavity during periods of coughing.

The need for such immobilizer becomes quite apparent when one considers that more than 170,000 heart bypass operations alone are performed in the United States annually.

Accordingly, it is an object of the present invention to provide a technique for instantaneously encircling the body in response to or in preparation for the onset of coughing, etc. to immobilize the chest or sternum or other encircled body party.

It is another object to provide a light-weight strap or harness which is normally worn comfortably as a loose vest or belt and is adapted to be instantaneously closed in preparation for or in response to the onset of coughing, sneezing, etc. to immobilize the chest and sternum or other body part.

In one aspect, the present invention involves a method for restraining a selected body part by providing a wrapping member such as a belt or strap having a pair of spaced gripping members; positioning the strap about the circumference of the particular body part; and applying force via the gripping members to shorten the circumference of the strap and tighten the strap about the body part.

In another aspect, the invention relates to a harness for immobilizing a body part comprising a first strap having first and second sections for wrapping around opposite sides of the body to encircle the body; a pair of support straps attached to the first strap at spaced points for passing over the shoulders of the individual to support and position the first strap along the body; and a pair of gripping members attached one to each section of the strap at spaced points such that when the first strap is in position, the gripping members are closely spaced to permit squeezing engagement to close the strap about the body.

In still other, alternative aspects, the harness and support straps may be formed as part of a unitary vest structure; or the shoulder support straps may be omitted and the immobilizing strap used on body limbs.

These and other aspects of my invention are described in detail with respect to the drawings in which:

FIG. 1 is a front perspective view of one embodiment of the harness or vest of the present invention showing the position of the harness on a human body;

FIG. 2 is a rear perspective view of the harness of FIG. 1;

FIG. 3 is a top view of the harness of FIG. 1 illustrating closure thereof by hand;

FIGS. 12 and 13 illustrate an alternative gripping member.

DETAILED DESCRIPTION

Figure 4:
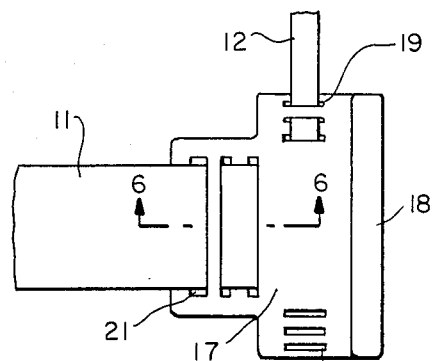
FIGS. 4–6 are front, bottom and partial longitudinal cross-sectional views, respectively, of one type of gripping member which is part of the immobilizer harness.

FIGS. 1 and 2 illustrate one embodiment 10 of my immobilizer in position supported on the shoulders of a human body. The immobilizer 10 comprises a relatively wide horizontal body strap 11 and a pair of narrower shoulder support straps 12—12. The straps can be made of any of a number of preferably light-weight, non-stretch materials such as canvas webbing, plastic, cloth or leather. The width of the straps will be readily varied to suit the particular need. However, suitable width dimensions for a chest/sternum immobilizer are four and one-half inches for the body strap and one and one-half inches for the shoulder straps 12.

The shoulder straps 12—12 are attached at one end to the rear of the body strap 11 at attachment points 15—15. The other end of each shoulder strap is secured to the front of the body strap 11, at or adjacent to the respective ends 13—13 of the body strap. Gripping handles 14—14 are attached at each end of the body strap 11. The length of the body strap and that of the shoulder straps are selected so that, in repose, the gripping members 14—14 are spaced apart several inches. Thus, and referring to FIG. 3, when the recuperating patient who is wearing the harness 10 desires to cough or sneeze, or senses the onset of coughing or sneezing, the handles 14—14 can be squeezed together by one or both hands to shorten the circumference of the body strap 11 and, as a consequence, tighten the body strap about the chest or abdomen to instantaneously and temporarily immobilize the chest and sternum. After the coughing, the handles 14—14 are released to release the immobilizing constraint.

This temporary immobilization of the chest or abdomen greatly reduces movement of the sternum, rib cage and, in so doing, greatly reduces pain. In addition, my own experience leads me to believe that this immobilization aids and quickens the healing process. At the same time, the chest or abdomen is normally not tightly bound by the harness, in accordance with the accepted medical practice of having the chest unbound to reduce the possibility of pneumonia and other complications.

Figure 5:
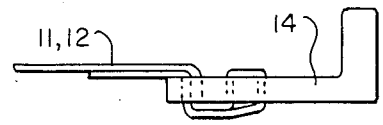
Figure 6:
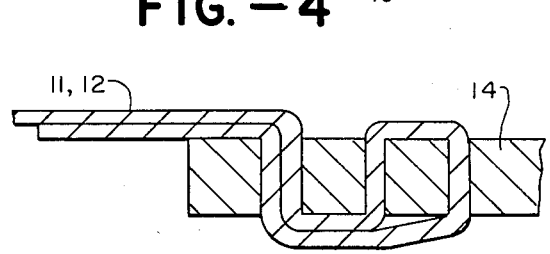

The handles or gripping members 14—14 can take various forms. A presently preferred version is shown in the front view of FIG. 4 and in the associated views in FIGS. 5 and 6. The handle 14 comprises a base plate 17 having an upwardly (outwardly) angled gripping projection 18. A plurality of slits 19—19 is formed at the top and bottom edges of the base plate, whereas another plurality of slits 21—21 is formed at the rear edge. The slits 19 and 21 permit secure, adjustable fastening of the shoulder strap 12 and the body strap 11 to the handle 14A, as shown in FIG. 6. The presence of slits 19 at the top and bottom edges permits the handle 14A to be used as either the right or left handle; only one set of slots 19 is used at a time. The looped strap attachment to the handle 14, which is shown in FIG. 6, allows the straps to be adjusted readily to different lengths to accommodate different individuals and/or different sized body parts. An alternative, streamlined gripping member or handle 14A is shown in FIGS. 12 and 13. Handle 14A includes an opening 28 which can be used in conjunction with projection 18A for closing the strap 11 about the selected body part. As shown in FIG. 13, in the embodiment 14A, single slits 19A and 21A are formed in the top and bottom edges and at the side edge of the handle for adjustably retaining the straps 11 or 12. Alternatively, a plurality of one or both of slits 19A and 21A can be used, in the manner of handle 14, FIG. 4.

Figure 7:
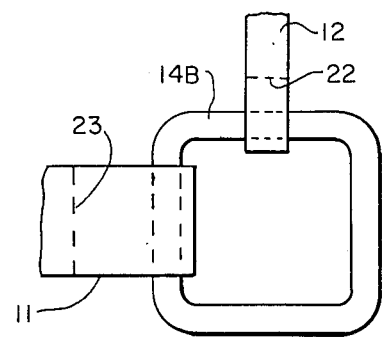
FIGS. 7 and 8 illustrate alternative approaches for fastening the body straps and shoulder straps.
Figure 8:
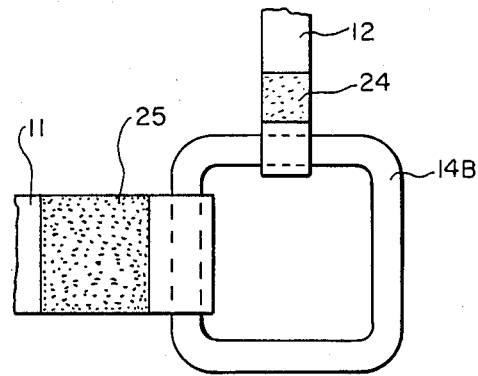

Alternative attachments for the body strap 11 and shoulder straps 12—12 are shown in FIGS. 7 and 8. In FIG. 7, handle 14B has the form of a closed loop or ring. The straps 11 and 12 are fastened to the handle 14B by folding back over the handle and sewing at 22 and 23. Alternatively, as shown in FIG. 8, the attachment can be separable and the length of the strap adjustable by using loop and hook fastening surfaces 24 and 25 (for example, Velcro TM). Other separable fasteners can be used including buttons and snap-on fastenings.

Figure 9:
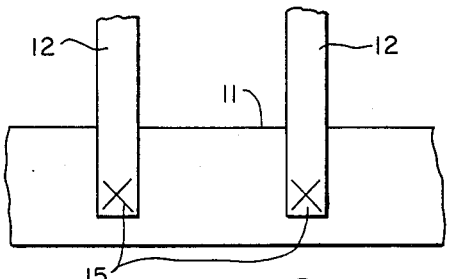
FIGS. 9–11 illustrate alternative approaches for attaching the shoulder straps to the body strap.
Figure 10:
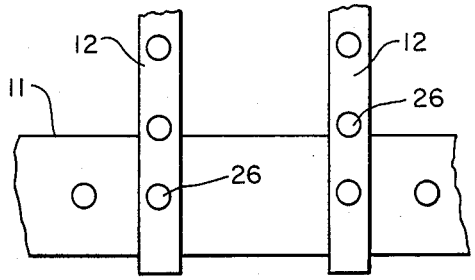
Figure 11:
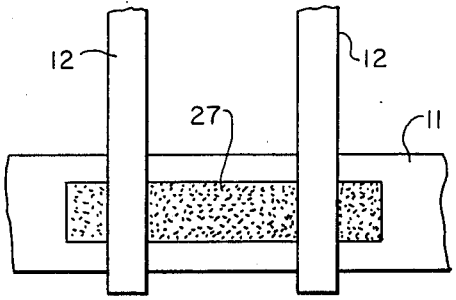

Similarly, the shoulder straps 12—12 can be joined to the body strap in either separable or non-separable, adjustable or non-adjustable fashion. For example, FIG. 9 illustrates non-adjustable attachment by sewing. FIG. 10 illustrates the use of spaced snaps 26—26 which permit adjustment of the length of the shoulder straps 12—12 and the spacing between the shoulder strap attachment points on the body strap 11. FIG. 11 illustrates a similarly versatile fastening approach using hook and loop type of fastening surfaces 27.

The harness straps can take various forms in addition to the body strap 11 and shoulder straps 12—12. For example, the harness may be embodied without shoulder straps, that is, as a body strap having handles 14—14. Such a harness is useful as an immobilizer for body parts such as arms and legs. Secondly, the body strap need not have an opening between "end sections 13—13", but could be attached as a loose-fitting belt which is tightened by the spaced handles 14—14. In this embodiment, the strap 11 could have overlapping ends which are secured by Velcro TM or other fasteners to provide the loose repose fitting. For some applications the strap 11 can be a continuous belt, i.e., without ends. As a third alternative, the body and shoulder straps may be formed as a one-piece vest with gripping members connected to the open ends of the vest.

Those skilled in the art will readily derive other embodiments which are within the spirit and scope of the present invention.

Having thus described preferred and alternative embodiments of my invention, what is claimed is:

1. A method for a person to temporarily immobilize a selected region of that person's own upper body such as the chest and sternum against percussive expansion, comprising providing an inelastic circumferential normally open body strap having a closed length approximating the circumference of the nonexpanded selected region but shorter than the expanded body region and having a pair of closely spaced handles; suspending the body strap from the shoulders with the handles positioned at the front of the chest and the open strap loosely encircling the major portion of the circumference of the selected region; at the onset of coughing or sneezing, forcibly engaging the handles to move the handles together to tighten the strap about the selected region to prevent percussive expansion of the chest during the coughing or sneezing; and after the coughing or sneezing, releasing the gripping members.

2. A harness configured to be positioned on and loosely about a selected region of a wearer's upper body such as the chest or abdomen for permitting the wearer to rapidly cinch the harness about the selected region to prevent percussive expansion of the selected region during coughing, sneezing and the like, comprising: a normally open inelastic first strap of selected length for wrapping around and loosely encircling a major portion of the nonexpanded selected body region and having a closed length approximating the circumference of the selected body region but shorter than the expanded body region; a pair of support straps attached to the first strap at spaced points for passing over the shoulders of the wearer to support and position the first strap at the selected region of the upper body, the support straps being of adjustable length to permit selectively positioning the first strap at different locations along the upper body and to accommodate bodies of different size; and a pair of handles attached to the first strap at spaced points such that when the first strap is in position on the body, the gripping handles are closely spaced at the front of the body for ready access and rapid use by the wearer for squeezing the handles together to close the first strap tightly about the selected body region and thereby prevent percussive expansion of the selected body region during coughing and the like; at least one of the handles being releasably attachable at a plurality of points along the first strap to adjust the circumference of the first strap.

3. A harness configured to be positioned on and loosely about a selected region of a wearer's upper body such as the chest or abdomen for permitting the wearer to rapidly cinch the harness about the selected region to prevent percussive expansion of the selected region during coughing, sneezing or the like, comprising:
  a normally opened inelastic first strap of selected length for wrapping around and loosely encircling the motor portion of the selected body region and having a closed length approximating the circumference of the nonexpanded selected body region and shorter than the expanded body region;
  a pair of support straps attached to the first strap at spaced points for passing over the shoulders of the wearer to support and position the first strap at and loosely encircling the selected region of the upper body; and
  a pair of handles attached to the first strap at spaced points such that when the first strap is in position on the body, the handles are closely spaced at the front of the body for ready access and rapid use by the wearer for squeezing the handles together to close the first strap tightly about the selected upper body region to thereby prevent percussive expansion of the selected upper body region during coughing, sneezing and the like.

4. The harness of claim 3 in which the first strap and the support straps comprise a unitary vest structure.

5. The harness of claim 2 or 3 in which at least one of the handles has slots at two adjacent sides thereof for adjustable attachment to the first strap and the adjacent shoulder strap.

6. The harness of claim 2 or 3 wherein the shoulder straps are releasably attachable to the first strap at a plurality of points along the shoulder straps and the first strap to accommodate selected body regions of different sizes.

* * * * *